(12) United States Patent
Lee

(10) Patent No.: US 11,969,515 B2
(45) Date of Patent: Apr. 30, 2024

(54) BUTTON MODULE HAVING A STERILIZATION FUNCTION

(71) Applicant: Jang Moon Lee, Namyangju-si (KR)

(72) Inventor: Jang Moon Lee, Namyangju-si (KR)

( * ) Notice: Subject to any disclaimer, the term of this patent is extended or adjusted under 35 U.S.C. 154(b) by 0 days.

(21) Appl. No.: 17/646,594

(22) Filed: Dec. 30, 2021

(65) Prior Publication Data
US 2022/0202974 A1 Jun. 30, 2022

(30) Foreign Application Priority Data
Dec. 31, 2020 (KR) .......................... 10-2020-0189546

(51) Int. Cl.
| | |
|---|---|
| A61L 2/10 | (2006.01) |
| A61L 2/26 | (2006.01) |
| H01H 13/14 | (2006.01) |
| H01H 13/20 | (2006.01) |
| H05K 7/14 | (2006.01) |

(52) U.S. Cl.
CPC ........ *A61L 2/10* (2013.01); *A61L 2/26* (2013.01); *H01H 13/14* (2013.01); *H01H 13/20* (2013.01); *H05K 7/1427* (2013.01); *A61L 2202/11* (2013.01); *A61L 2202/14* (2013.01)

(58) Field of Classification Search
CPC ...... B66B 2201/103; B66B 2201/4615; B66B 2201/463; B66B 1/52; A61L 2202/11; A61L 2202/14; A61L 2202/10; A61L 2202/26; A61L 2/10; A61L 2/26; H05K 7/142; H05K 7/14; H05K 7/1427; H01H 13/14; H01H 13/20; H01H 13/70; H01H 1/18; H01H 1/36; H01H 1/60; H01H 2231/03

USPC ........................................................ 200/341
See application file for complete search history.

(56) References Cited

U.S. PATENT DOCUMENTS

| | | | | |
|---|---|---|---|---|
| 6,111,401 A | * | 8/2000 | Mierzwinski | ........... G01P 3/488 |
| | | | | 324/207.2 |
| 8,080,316 B2 | * | 12/2011 | Mangiardi | ............. C08J 7/0427 |
| | | | | 428/323 |

FOREIGN PATENT DOCUMENTS

| | | |
|---|---|---|
| JP | 2011116536 A | 6/2011 |
| KR | 1020110072601 | 5/2013 |
| KR | 101299569 B1 | 8/2013 |
| KR | 101431515 B1 | 8/2014 |
| KR | 1020190052976 | 10/2019 |
| KR | 102186388 B1 | 12/2020 |

* cited by examiner

*Primary Examiner* — Anthony R Jimenez
(74) *Attorney, Agent, or Firm* — Stetina Brunda Garred & Brucker

(57) ABSTRACT

This embodiment relates to a button module having a sterilization function. The button module according to one aspect comprises: a cover including an opening; a housing being coupled to the cover; a button body disposed inside the housing, including a first body and a second body selectively exposed to the outside through the opening; a rotation shaft for rotating the button body; a printed circuit board disposed at a rear side of the button body, the printed circuit board including a switch and a germicidal lamp irradiating light toward the button body; and an elastic member disposed between the rotation shaft and the first body and between the rotation shaft and the second body.

10 Claims, 12 Drawing Sheets

BUTTON MODULE HAVING A STERILIZATION FUNCTION

CROSS-REFERENCE TO RELATED APPLICATIONS

This application claims priority to Korean Patent Application No. 10-2020-0189546 filed on Dec. 31, 2020, the entire disclosure of which is expressly incorporated herein by reference.

STATEMENT RE: FEDERALLY SPONSORED RESEARCH/DEVELOPMENT

Not Applicable

BACKGROUND

Technical Field

This embodiment relates to a button module having a sterilization function.

Background Art

As an input means of a user control command, the type of a button module can be divided into a push method or a touch method. Both the push method and the touch method may be operated through contact with the body of a user. However, since the user's hand is in direct contact with the button surface, there is an unsanitary problem in which bacteria are infected or transmitted.

For example, since a button module placed in a bus for stop notification is used by unspecified number of people, there is a concern of the spread of infectious diseases (COVID-19, etc.).

BRIEF SUMMARY

Technical Subject

An object of the present invention is to provide a button module capable of securing user's safety by sterilizing button every time it is operated by a user.

Technical Solution

A button module according to the present embodiment includes a cover including an opening; a housing coupled to the cover; a button body disposed in the housing and including a first body and a second body selectively exposed to the outside through the opening; a rotation shaft for rotating the button body; a printed circuit board disposed inside the housing, the printed circuit board including a switch and a germicidal lamp irradiating light toward the button body; and an elastic member disposed between the rotation shaft and the first body and between the rotation shaft and the second body.

Advantageous Effects

By partitioning the outer surface of the button module into a use surface and a use standby surface through this embodiment, the sterilization surface is replaced so that the sterilization surface is exposed to the outside every time the user operates it so that there is an advantage in that the spread of disease due to bacterial infection or transmission is prevented.

BRIEF DESCRIPTION OF THE DRAWINGS

These and other features and advantages of the various embodiments disclosed herein will be better understood with respect to the following description and drawings, in which like numbers refer to like parts throughout, and in which.

DETAILED DESCRIPTION

Hereinafter, preferred embodiments of the present invention will be described in detail with reference to the accompanying drawings.

However, the technical idea of the present invention is not limited to some embodiments to be described, but may be implemented in various forms, and within the scope of the technical idea of the present invention, one or more of the constituent elements may be selectively combined or substituted between embodiments.

In addition, the terms (including technical and scientific terms) used in the embodiments of the present invention, unless explicitly defined and described, can be interpreted as a meaning that can be generally understood by a person skilled in the art, and commonly used terms such as terms defined in the dictionary may be interpreted in consideration of the meaning of the context of the related technology.

In addition, terms used in the present specification are for describing embodiments and are not intended to limit the present invention.

In the present specification, the singular form may include the plural form unless specifically stated in the phrase, and when described as "at least one (or more than one) of A and B and C", it may include one or more of all combinations that can be combined with A, B, and C.

In addition, in describing the components of the embodiment of the present invention, terms such as first, second, A, B, (a), and (b) may be used. These terms are merely intended to distinguish the components from other components, and the terms do not limit the nature, order or sequence of the components.

And, when a component is described as being 'connected', 'coupled' or 'interconnected' to another component, the component is not only directly connected, coupled or interconnected to the other component, but may also include cases of being 'connected', 'coupled', or 'interconnected' due that another component between that other components.

In addition, when described as being formed or arranged in "on (above)" or "below (under)" of each component, "on (above)" or "below (under)" means that it includes not only the case where the two components are directly in contact with, but also the case where one or more other components are formed or arranged between the two components. In addition, when expressed as "on (above)" or "below (under)", the meaning of not only an upward direction but also a downward direction based on one component may be included.

Figure 1:
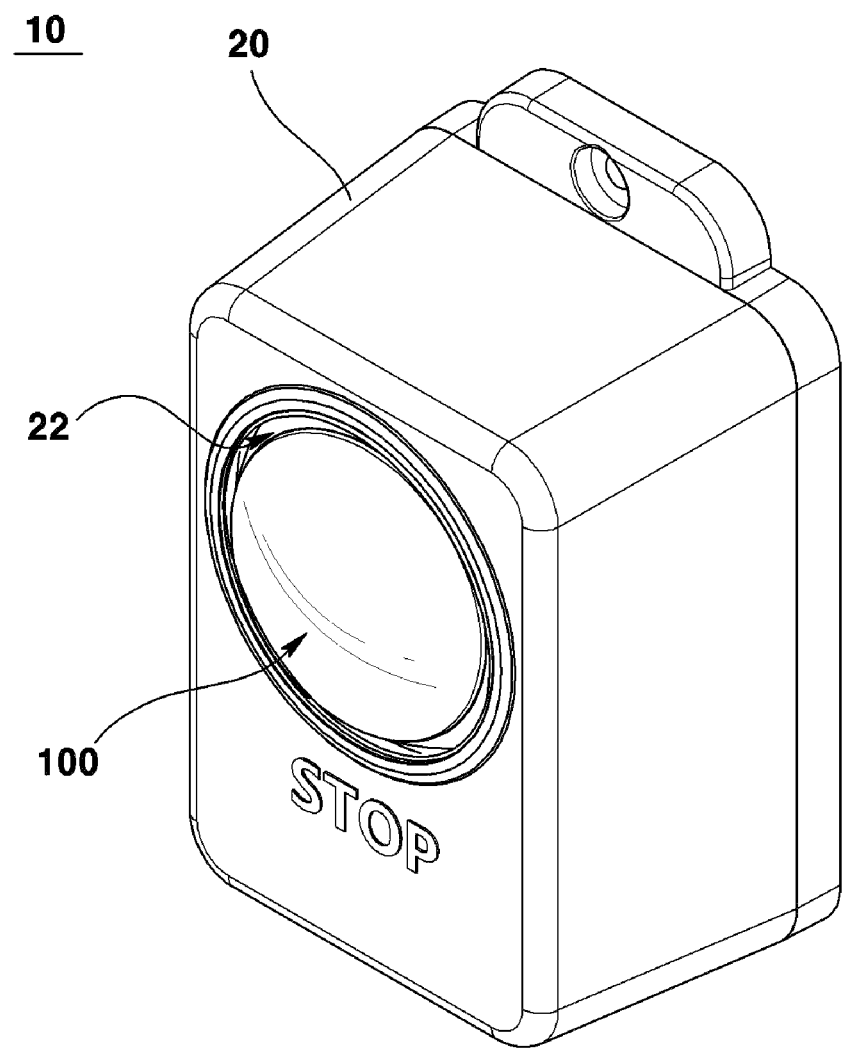
FIG. 1 is an exemplary view of a button module according to an embodiment of the present invention.
Figure 2:
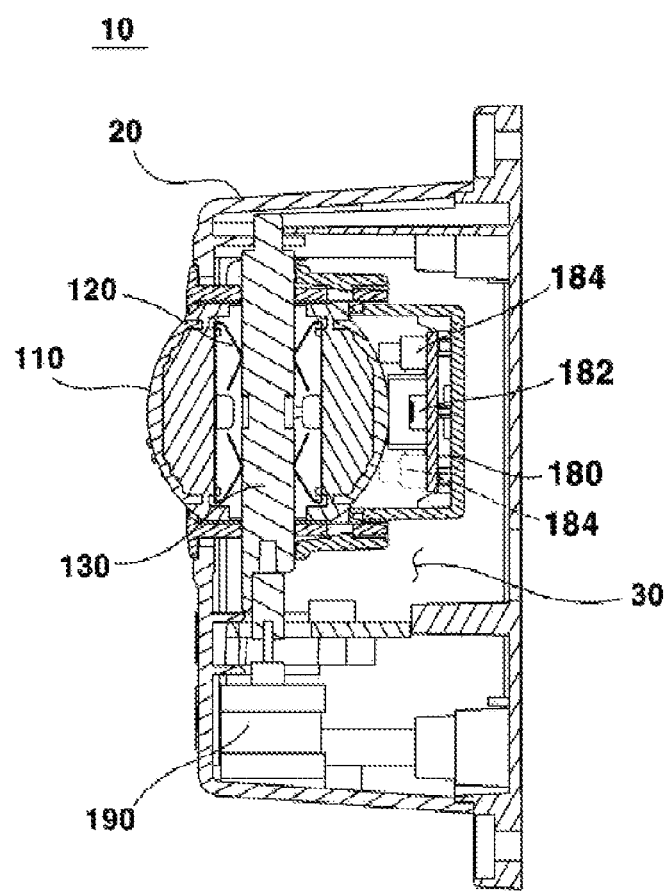
FIG. 2 is a side cross-sectional view of FIG. 1.
Figure 3:
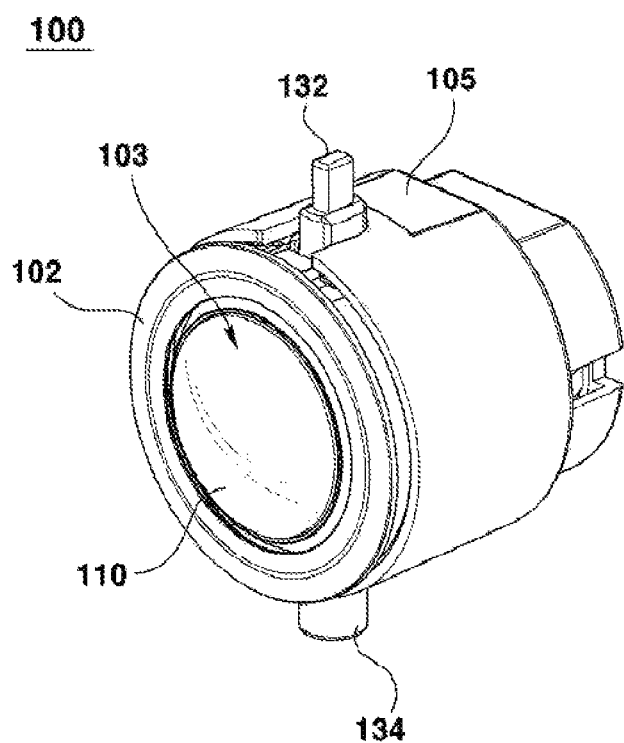
FIG. 3 is a perspective view of a button module according to an embodiment of the present invention.
Figure 4:
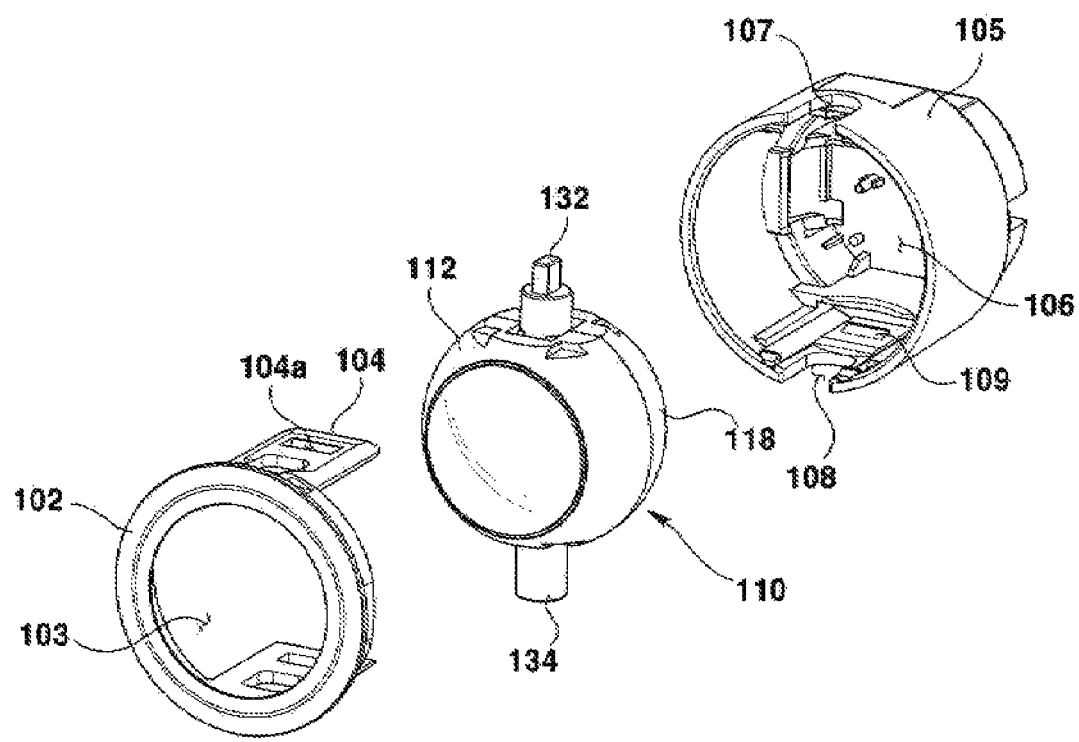
FIG. 4 is a first exploded perspective view of a button module according to an embodiment of the present invention.
Figure 5:
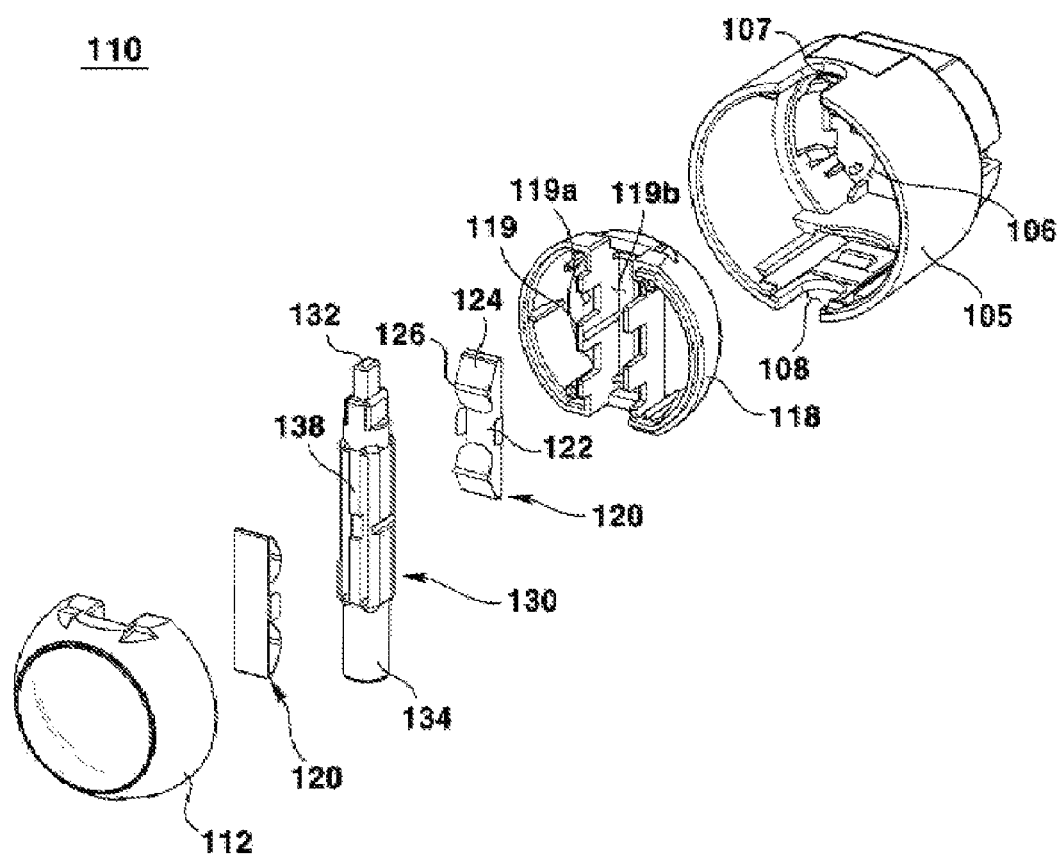
FIG. 5 is a second exploded perspective view of a button module according to an embodiment of the present invention.
Figure 6:
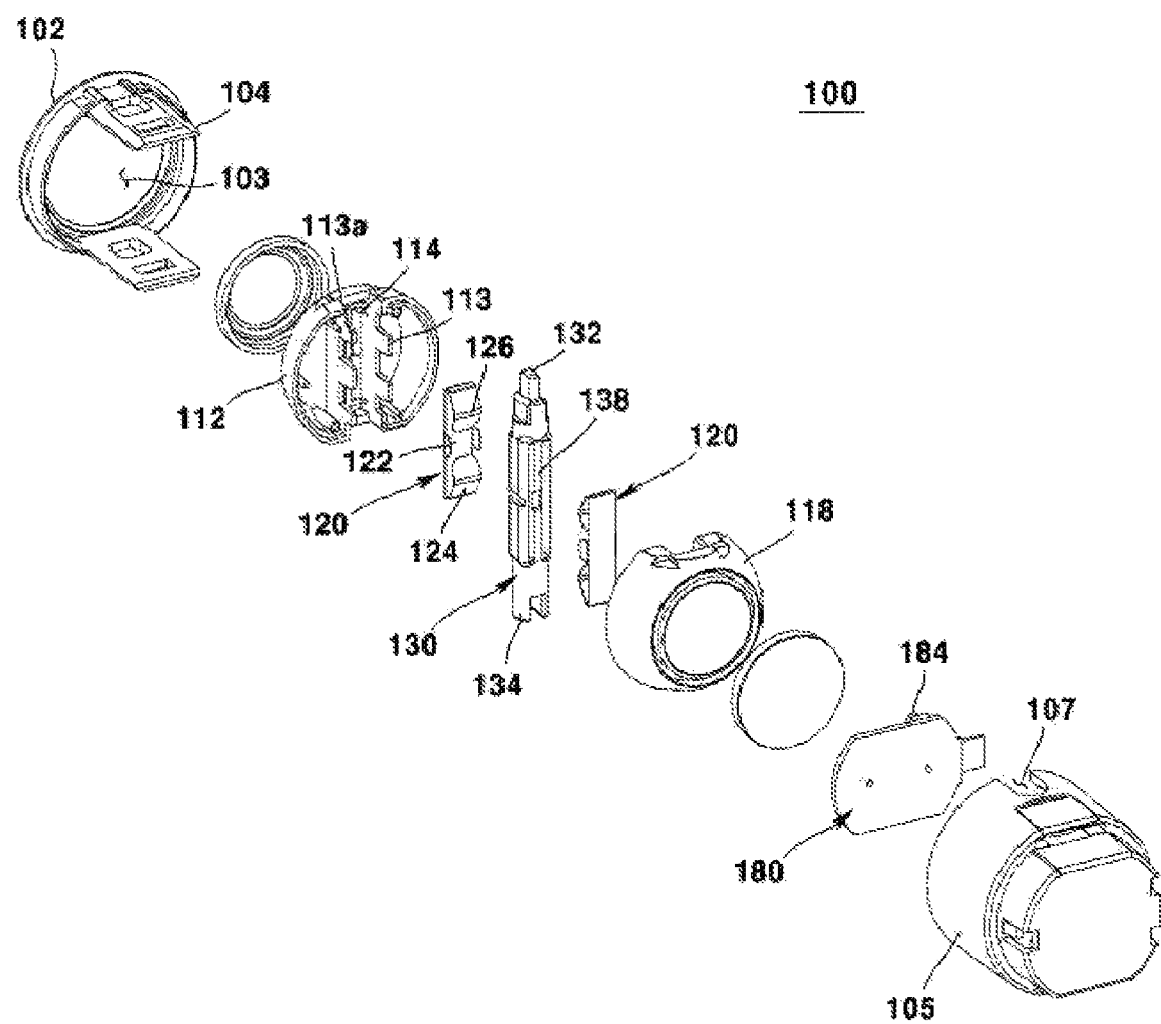
FIG. 6 is a third exploded perspective view of a button module according to an embodiment of the present invention.
Figure 7:
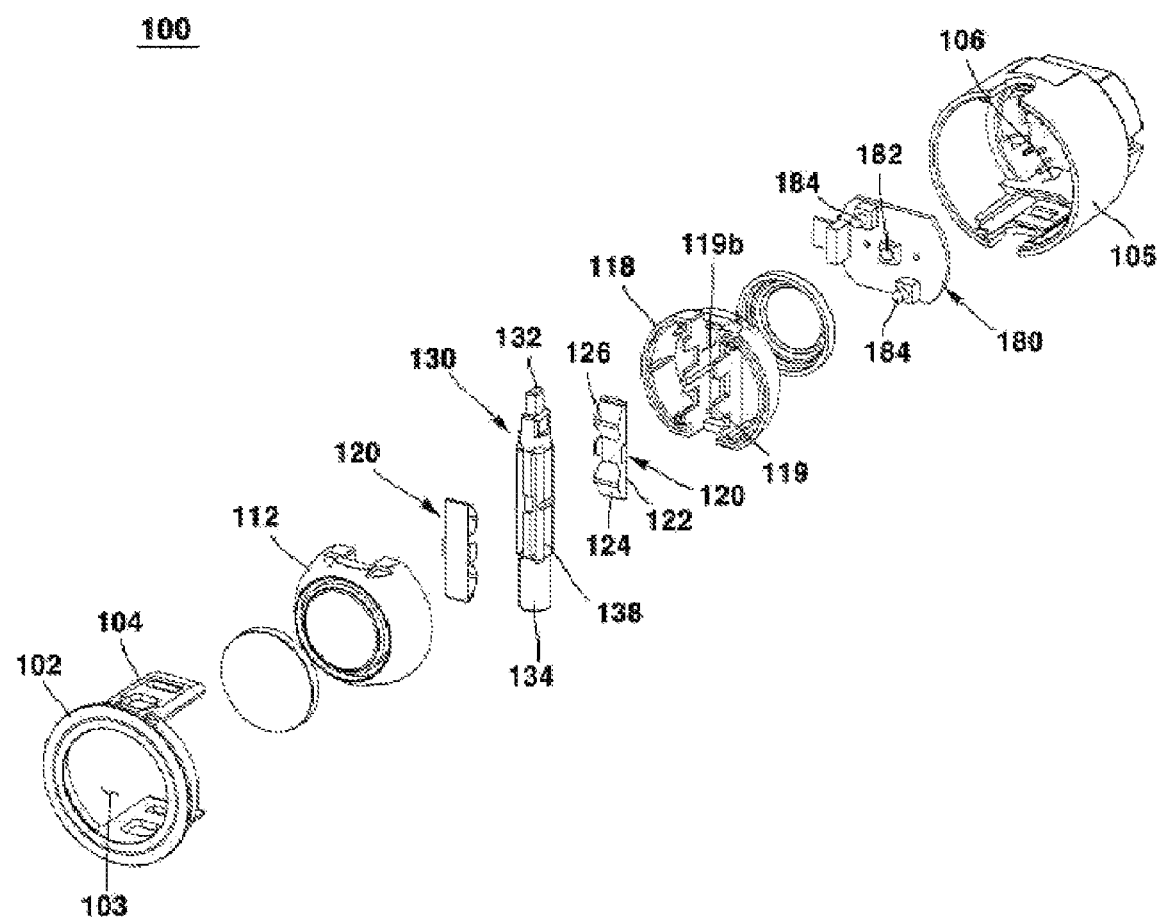
FIG. 7 is a fourth exploded perspective view of a button module according to an embodiment of the present invention.
Figure 8:
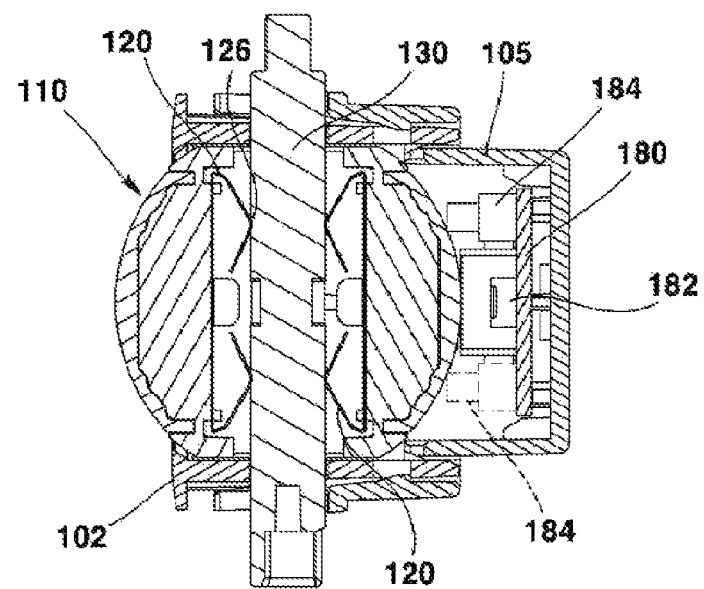
FIG. 8 is a side cross-sectional view of a button module according to an embodiment of the present invention.
Figure 9:
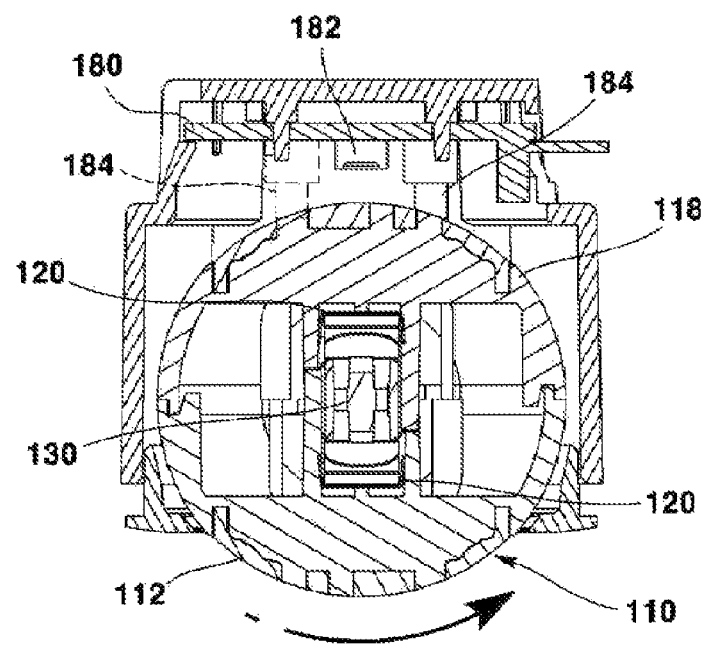
FIG. 9 is a cross-sectional view of a button module according to an embodiment of the present invention.
Figure 10:
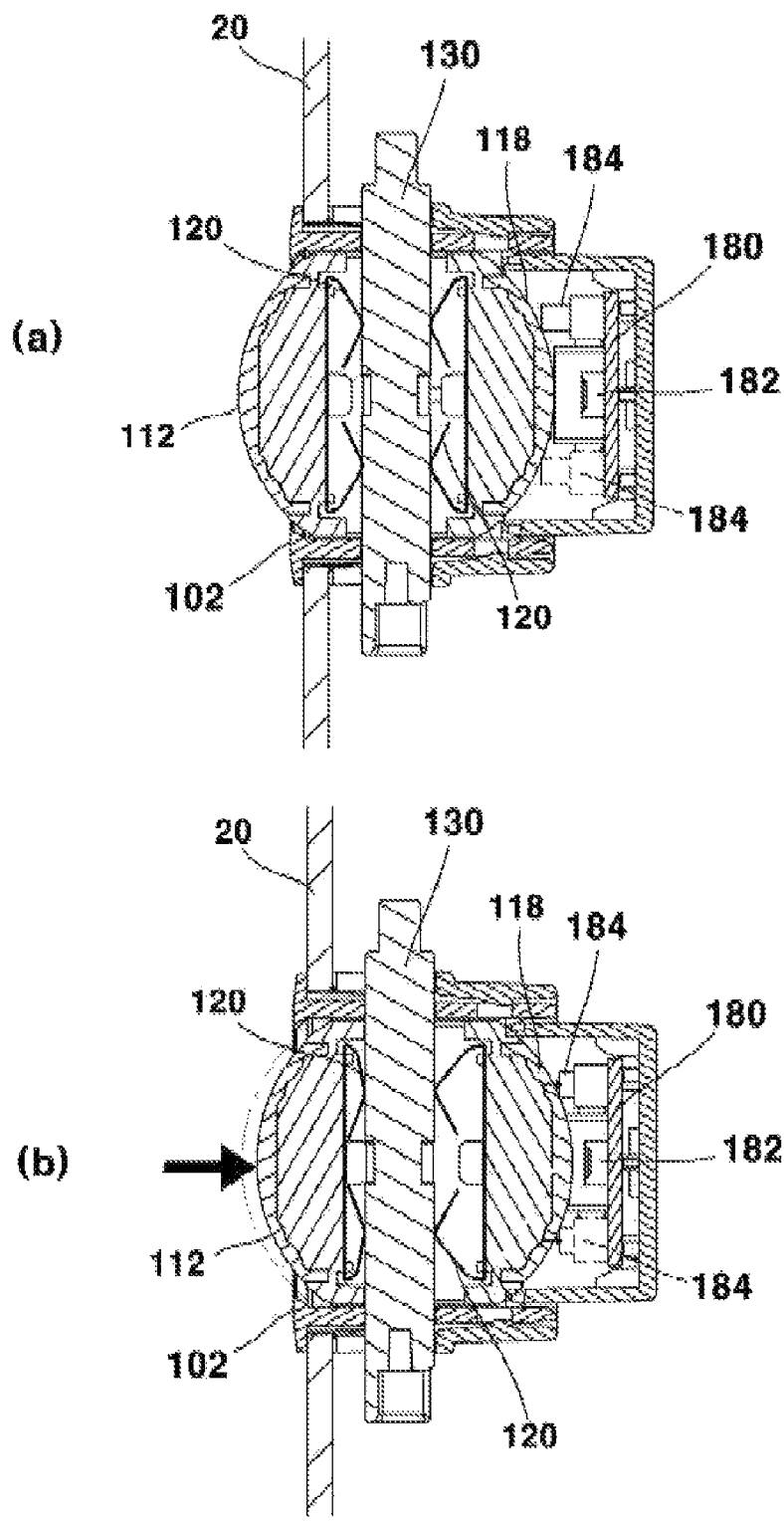
FIG. 10 is a cross-sectional view for explaining an operation process of a button module according to an embodiment of the present invention.
Figure 11:
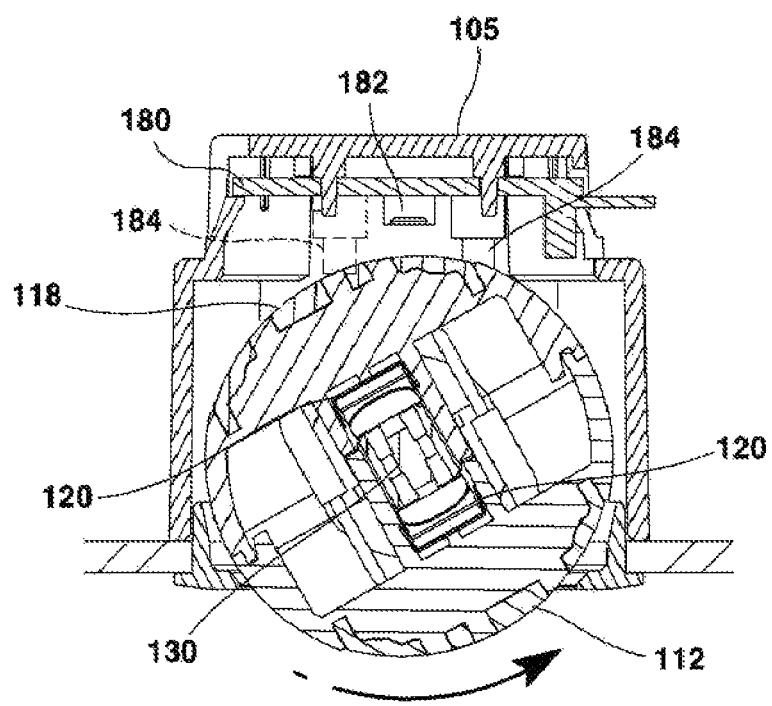
FIG. 11 is a cross-sectional view illustrating a process in which a use part and a use standby part of a button module are replaced according to an embodiment of the present invention.
Figure 12:
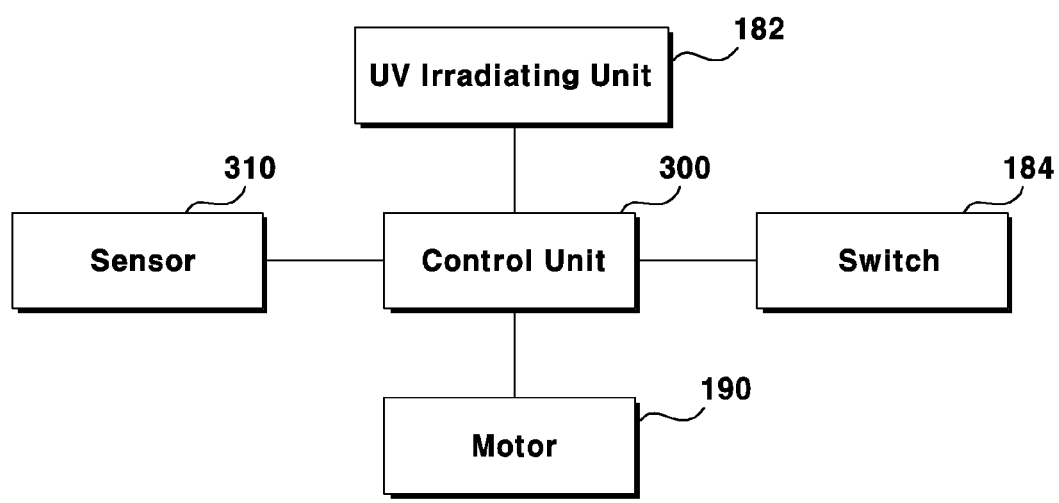
FIG. 12 is a block diagram of a button module according to an embodiment of the present invention.

FIG. 1 is an exemplary view of a button module according to an embodiment of the present invention, FIG. 2 is a side cross-sectional view of FIG. 1, FIG. 3 is a perspective view of a button module according to an embodiment of the present invention, FIG. 4 is a first exploded perspective view of a button module according to an embodiment of the present invention, FIG. 5 is a second exploded perspective view of a button module according to an embodiment of the present invention, FIG. 6 is a third exploded perspective view of a button module according to an embodiment of the present invention, FIG. 7 is a fourth exploded perspective view of a button module according to an embodiment of the present invention, FIG. 8 is a side cross-sectional view of a button module according to an embodiment of the present invention, FIG. 9 is a cross-sectional view of a button module according to an embodiment of the present invention, FIG. 10 is a cross-sectional view for explaining an operation process of a button module according to an embodiment of the present invention, FIG. 11 is a cross-sectional view illustrating a process in which a use part and a use standby part of a button module are replaced according to an embodiment of the present invention, and FIG. 12 is a block diagram of a button module according to an embodiment of the present invention.

Referring to FIGS. 1 to 12, a button module 100 according to the present embodiment may be disposed inside the housing 20 forming an outer shape. The housing 20 may include an opening 22 for exposing at least a portion of the button module 100. A space 30 may be formed inside the housing 20 to accommodate a plurality of components for driving the button module 100.

The button module 100 may be implemented as a push switch method through a button and a touch switch method, but hereinafter, the button module 100 will be described as an example of a push switch method. In addition, in this embodiment, the button module 100 is exemplified to be disposed inside the housing 20 forming the outer shape, but it is not limited thereto, and it may be configured in a way that the button module 100 is embedded in a wall having an opening so that at least a portion thereof is exposed to the outside.

The button module 100 may be exposed to the outside through the opening 22. The button module 100 is operated by a user, and the user can input a control command by pushing an area exposed to the outside through the opening 22.

The button module 100 may include a housing 105, a cover 102, a button body 110, an elastic member 120, a rotation shaft 130, and a printed circuit board 180.

The housing 105 and the cover 102 form an outer shape of the button module 100 and may be coupled to each other. A space 106 for accommodating the button body 110 and the printed circuit board 180 may be formed inside the housing 105. The cover 102 may be disposed inside the opening 22. The front surface of the cover 102 may be exposed to the outside. An opening 103 for exposing the button body 110 to the outside may be formed in the center of the cover 102 to pass through the rear surface from the front surface.

A rib 109 being protruded inward may be formed on an inner surface of the space 106 inside the housing 105. In addition, the cover 102 may include a coupling part 104 being protruded rearward from a ring-shaped region and has a hole 104a to be coupled to the rib 109. Accordingly, the housing 105 and the cover 102 may be coupled to each other by a hook coupling structure of the rib 109 and the hole 104a. An inclined surface is disposed on an upper surface of the rib 109, so that the coupling part 104 can be easily slidingly moved.

Holes 107 and 108 may be respectively disposed on an upper and a lower surface of the housing 105 so that a rotation shaft 130 to be described later passes therethrough. Similarly, a hole may be disposed in a region of the coupling part 104 being overlapped with the holes 107 and 108 in an up and down direction so that the rotation shaft 130 may penetrate therethrough.

The button body 110 is disposed in the housing 105, and at least a portion thereof may be exposed to the outside through an opening 103 formed in the cover 102. The button body 110 may be formed in a sphere shape. The button body 110 may be formed by coupling a first body 112 and a second body 118. The button module 10 according to the present embodiment is characterized by preventing the spread of disease due to bacterial infection or transmission by dividing the floor selection button 100, that is used continuously and repeatedly by an unspecified number of visiting people, into a use surface and a use standby surface, and automatically replacing them alternately each time they are being used. Accordingly, the surface of the button body 110 exposed through the opening 103 may be replaced whenever a user operates. For example, when the user operates with an outer surface of the first body 112 exposed through the opening 103, the control unit 300, which will be described later, rotates the button body 110 so that an outer surface of the second body 118 may be exposed. Similarly, when the user makes contact with an outer surface of the second body 118, the control unit 300 may rotate the button body 110 to expose an outer surface of the first body 112.

The first body 112 and the second body 118 may each have a hemispherical shape.

A plurality of first ribs 113 being protruded inward may be formed on an inner surface of the first body 112 being coupled to the second body 118. The plurality of first ribs 113 may be disposed to be spaced apart from each other, and a first rib groove 113a may be disposed therebetween.

A plurality of second ribs 119 being protruded inward may be formed on an inner surface of the second body 118 coupled to the first body 112. The plurality of second ribs 119 may be disposed to be spaced apart from each other, and a second rib groove 119a may be disposed therebetween.

Therefore, when the first body 112 and the second body 118 are coupled, the first rib 113 is coupled to the second rib groove 119a, and the second rib 119 may be coupled to the first rib groove 113a.

Meanwhile, on an inner surface of the first body 112 and an inner surface of the second body 118, a plurality of disposition regions of the first rib 113 and the second rib 119 may be provided, respectively, and the coupling grooves 114 and 119b may be respectively disposed between the disposition regions of the plurality of the first ribs 113 and the second ribs 119 so that the rotation shaft 13 is coupled.

A hole through which the rotation shaft 130 is penetrated may be disposed on an upper surface and a lower surface of the button body 110 corresponding to the region in which the coupling grooves 114 and 119b are formed. The hole may be an area being formed by upper and lower ends of the coupling grooves 114 and 119b.

Meanwhile, in the present embodiment, the button body 110 has been described to be a spherical shape as an example, but it is not limited thereto, and for a sense of unity with the cover 102, an outer surface region of the button body 110 being exposed through the opening 103 may be formed to be a planar surface.

In addition, a display panel indicating control information related to the control of the button module 100 may be attached to an outer surface of the first body 112 and an outer surface of the second body 118, respectively. For example, a number for indicating the number of floors may be described on the display panel.

The rotation shaft 130 may be disposed at the center of the button body 110. The rotation shaft 130 may be disposed between the first body 112 and the second body 118. The upper and lower ends of the rotation shaft 130 may be disposed to be protruded upward and downward of the button body 110, respectively. The rotation shaft 130 may be connected to a drive motor 190 to be described later and rotate together by driving the drive motor 190. The button body 110 may also be rotated by the rotation of the rotation shaft 130. The area of the rotation shaft 130 accommodated in the button body 110 may have a rectangular cross-sectional shape. Accordingly, when the rotation shaft 130 is rotated, the outer surface of the rotation shaft 130 and the inner surface of the coupling grooves 114 and 119b come into contact with each other, so that the button body 110 can rotate together.

Figure 13:
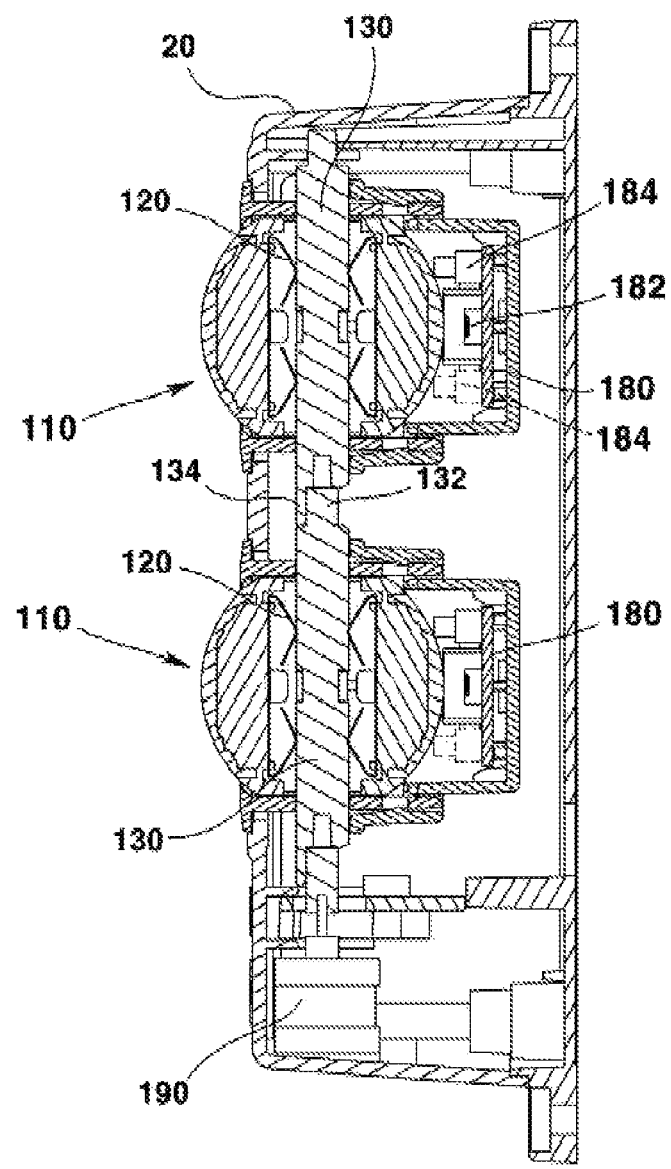
FIG. 13 is a modified embodiment of a button module according to an embodiment of the present invention.

As in FIG. 13, the button module 100 may be provided in plurality in a single housing. The plurality of button modules 100 may be disposed in an up and down direction. The plurality of button modules 100 may be coupled to each other through the rotation shaft 130 of each adjacent button module 100.

In detail, a protruded portion 132 protruding upward may be formed at an upper end of the rotation shaft 130 and a groove 134 more concave upward than other regions may be formed at a lower end of the rotation shaft 130. Therefore, a plurality of button modules 100 disposed in an up and down direction may form a complementary bonding structure when the protruded portion 132 of the button module 100 disposed on a lower portion is being coupled to the groove 134 of the button module 100 disposed on an upper portion.

At this time, the rotation shafts 130 of the plurality of button modules 100 are disposed to be a common shaft, and can be rotated together by the driving of the drive motor 190.

The elastic member 120 may be disposed between the rotation shaft 130 and the first body 112 and between the rotation shaft 130 and the second body 118. In a state in which the button body 110 is being pushed by the user, the elastic member 120 may provide an elastic force to move the button body 110 to its original position.

In detail, the elastic member 120 is provided in plurality and can be disposed in each of a first coupling groove 114 disposed on an inner surface of the first body 112, and a second coupling groove 119b disposed on an inner surface of the second body 118. The elastic member 120 may include an outer surface portion 122 and an inner surface portion 124. The outer surface portion 122 is formed in a plate shape, and may be selectively in contact with bottom surfaces of the coupling grooves 112 and 119b. The inner surface portion 124 is disposed at an inner side of the outer surface portion 122 and may be selectively in contact with the outer surface of the rotation shaft 130. The inner surface portion 124 may be provided in plurality, and may be disposed to be spaced apart from each other by a predetermined distance in an up and down direction. The inner surface portion 124 may be extended from upper and lower ends of the outer surface portion 122. At least a portion of the inner surface portion 124 may be formed with a bent portion 126 being protruded inward. The elastic member 120 may be in contact with an outer surface of the rotation shaft 130 through the bent portion 126. The elastic member 120 may be formed of a metal material to provide an elastic force. That is, the elastic member 120 may provide an elastic force to press the button body 110 outward with respect to the rotation shaft 130.

In detail, as shown in FIG. 11, when the area of the button body 110 exposed through the opening 103 is the first body 112, when the first body 112 is pushed by the user, the button body 110 may be moved to be closer to the printed circuit board 180, which will be described later. At this time, since the rotation shaft 130 is fixed, by the movement of the button body 110, the relative position of the rotation shaft 130 with respect to the button body 110 may be changed inside the coupling grooves 114 and 119b. Meanwhile, the elastic member 120 may be pressed by the movement of the button body 110, and the inner surface portion 124 may be compressed such that the distance to the outer surface portion 122 to be closer. Accordingly, when the user's external force is removed, the button body 110 may be restored to its original position by the elastic force of the elastic member 120.

The printed circuit board 180 may be disposed in a space inside the housing 105. The printed circuit board 180 may be formed in a plate shape. A germicidal lamp 182 and a switch 184 may be disposed on one surface of the printed circuit board 180 facing the button body 110.

The germicidal lamp 182 is disposed in the center of one surface of the printed circuit board 180, and may radiate light toward the button body 110. The outer surface of the button body 110 may be sterilized by light irradiation of the germicidal lamp 182. The light irradiated from the germicidal lamp 182 may be ultraviolet light. Therefore, by the rotation of the button body 110, the button body 110 may be partitioned into a use standby surface defined as the outer surface of the first body 112 or the second body 118 and a use surface defined as the second body 118 or the first body 112, and among them, the use standby surface is disinfected through the germicidal lamp 182 so that the disinfected surface can be exposed through the opening 103 when the button body 110 is re-rotated.

The switch 184 may be provided in plurality and disposed to face each other with respect to the germicidal lamp 182. The switch 184 may be called an electric switch. The switch 184 may be disposed to be protruded outward so that the distance to the button body 110 is relatively closer than that to the germicidal lamp 182. In this embodiment, the plurality of switches 184 are exemplified to be respectively disposed in the corner regions of the printed circuit board 180, but is not limited thereto, and the plurality of switches 184 may be disposed on both sides of the germicidal lamp 182 to be spaced apart from each other by a predetermined distance. When pressure is applied to the plurality of switches 184 when the button body 110 is being pushed by a user, a control command can be inputted to the control unit 300, which will be described later.

The button module 100 may include a driving motor 190. The drive motor 190 may be a step motor. The drive motor 190 may be coupled to the rotation shaft 130 to rotate the rotation shaft 130 by driving.

And, as in the modified embodiment of FIG. 13, when the button module 100 is provided in plurality, rotation shafts 130 of the plurality of button modules 100 are coupled to each other to form a common shaft to be rotated together by driving. At this time, the drive motor 190 may be coupled to transmit a driving force to the rotation shaft 130 disposed at the bottommost end among the plurality of button modules 100.

A sensor 310 (refer to FIG. 13) may be disposed between the drive motor 190 and the button module 100. A bracket (not shown) for disposing the sensor 310 on an upper surface or a lower surface may be provided between the drive motor 190 and the button module 100. In addition, a guide (not shown) being protruded radially outwardly and selectively contacting the sensor 310 by rotation may be provided on an outer circumferential surface of the rotation shaft 130. According to the present embodiment, the button body 110 may be rotated 180 degrees every time the user manipulates it in a clockwise or counterclockwise direction. To control this, when the guide is in contact with the sensor 310 according to the rotation of the rotation shaft 130, the driving of the drive motor 190 may be stopped. Accordingly, the position of the sensor 310 and the guide may be set to an appropriate region for adjusting the rotation angle of the button body 110.

Hereinafter, an operation process of the button module according to the present embodiment will be described.

First, a use surface of the button body 110 exposed through the opening 103 may be pushed by a user. The switch 184 is pushed when the button body 110 is being pushed, and the control unit 300 may drive the elevator according to a control command initiated by the user.

Next, the control unit 300 may rotate the button body 110 by driving the drive motor 190 to replace the use surface and the use standby surface of the button body 110. As previously described, the button body 110 may be rotated 180 degrees, and accordingly, a use surface pushed by a user (for example, an outer surface of the first body 112) may be replaced by a use standby surface (for example, an outer surface of the second body 118) sterilized through the germicidal lamp 182. Accordingly, when a new user boards, the surface of the button body 110 exposed through the opening 103 may be a use standby surface sterilized through the germicidal lamp 182. And, a use surface pushed by a previous user may be sterilized by the operation of the germicidal lamp 182.

According to the structure as described above, by partitioning an outer surface of a button module into a use surface and a use standby surface so that a sterilized surface is exposed to the outside every time when the user operates it, so that there is an advantage in that it can prevent the spread of disease due to bacterial infection or transmission.

In the above description, it is described that all the components constituting the embodiments of the present invention are combined or operated in one, but the present invention is not necessarily limited to these embodiments. In other words, within the scope of the present invention, all of the components may be selectively operated in combination with one or more. In addition, the terms "comprise", "include" or "having" described above mean that the corresponding component may be inherent unless specifically stated otherwise, and thus it should be construed that it does not exclude other components, but further include other components instead. All terms, including technical and scientific terms, have the same meaning as commonly understood by one of ordinary skill in the art unless otherwise defined. Terms used generally, such as terms defined in a dictionary, should be interpreted to coincide with the contextual meaning of the related art, and shall not be interpreted in an ideal or excessively formal sense unless explicitly defined in the present invention.

The above description is merely illustrative of the technical idea of the present invention, and those skilled in the art to which the present invention pertains may make various modifications and changes without departing from the essential characteristics of the present invention. Therefore, the embodiments disclosed in the present invention are not intended to limit the technical idea of the present invention but to describe the present invention, and the scope of the technical idea of the present invention is not limited by these embodiments. The protection scope of the present invention should be interpreted by the following claims, and all technical ideas within the equivalent scope should be interpreted as being included in the scope of the present invention.

What is claimed is:

1. A button module comprising:
   a cover including an opening;
   a housing being coupled to the cover;
   a button body disposed inside the housing, including a first body and a second body selectively exposed to an outside of the cover through the opening;
   a rotation shaft for rotating the button body;
   a printed circuit board disposed at a rear side of the button body, the printed circuit board including a switch and a germicidal lamp irradiating light toward the button body; and
   an elastic member disposed at least one of between the rotation shaft and the first body and between the rotation shaft and the second body,
   wherein a plurality of first ribs being protruded inwardly and a first rib groove disposed between the plurality of first ribs are formed on an inner surface of the first body, and
   wherein on an inner surface of the second body, a plurality of second ribs being protruded inwardly and coupled to the first rib groove, and a second rib groove disposed between the plurality of second ribs, to which the plurality of first ribs are coupled, are formed.

2. The button module according to claim 1, wherein upper and lower ends of the rotation shaft are disposed to be protruded upward and downward of the button module, respectively.

3. The button module according to claim 1, comprising:
   a drive motor for rotating the rotation shaft,
   wherein the drive motor is a step motor.

4. The button module according to claim 1, wherein the switch is disposed closer to the button body than the germicidal lamp.

5. The button module according to claim 1, wherein an outer surface of the first body or the second body exposed to the outside through the opening is a planar surface.

6. The button module according to claim 1, wherein a guide being protruded radially outwardly from an outer circumferential surface of the rotation shaft and a sensor selectively contacting the guide are included, and
   wherein a control unit stops the rotation of the rotation shaft when the guide and the sensor are in contact with each other.

7. The button module according to claim 1, wherein the button body has a shape of a sphere.

8. The button module according to claim 1, wherein on an inner surface of the first body and an inner surface of the second body, coupling grooves for accommodating at least a portion of the elastic member and the rotation shaft are respectively disposed.

9. The button module according to claim 8, wherein the elastic member includes an outer surface portion in contact with a bottom surface of the coupling groove, and an inner surface portion disposed inside the outer surface portion and in contact with an outer surface of the rotation shaft, and wherein the elastic member provides an elastic force to apply pressure on the button body.

10. A button module comprising:
   a cover including an opening;
   a housing being coupled to the cover;
   a button body disposed inside the housing, including a first body and a second body selectively exposed to an outside of the cover through the opening;
   a rotation shaft for rotating the button body;
   a printed circuit board disposed at a rear side of the button body, the printed circuit board including a switch and a germicidal lamp irradiating light toward the button body; and
   an elastic member disposed at least one of between the rotation shaft and the first body and between the rotation shaft and the second body,
   wherein an outer surface of the first body or the second body exposed to the outside of the cover through the opening is a planar surface.

* * * * *